United States Patent [19]

Truong et al.

[11] Patent Number: 5,556,875
[45] Date of Patent: Sep. 17, 1996

[54] 1,2-DITHIIN ANTIINFECTIVE AGENTS

[75] Inventors: Thien V. Truong, Emeryville; Donald E. Bierer; Jeffrey M. Dener, both of Daly City; Richard Hector; Michael S. Tempesta, both of Moss Beach, all of Calif.; Bernard Loev, Scarsdale, N.Y.; Wu Yang; Masato Koreeda, both of Ann Arbor, Mich.

[73] Assignees: Shaman Pharmaceuticals, Inc., South San Francisco, Calif.; The Regents of the University of Michigan, Ann Arbor, Mich.

[21] Appl. No.: 110,917

[22] Filed: Aug. 24, 1995

[51] Int. Cl.$^6$ ............ A61K 31/385; C07D 339/08
[52] U.S. Cl. ............ 514/436; 549/14; 549/20; 549/22
[58] Field of Search ............ 514/436; 549/14, 549/20

[56] References Cited

U.S. PATENT DOCUMENTS

| | | | |
|---|---|---|---|
| 4,659,733 | 4/1987 | DuPriest et al. | 514/436 |
| 5,202,348 | 4/1993 | Towers et al. | 514/436 |

FOREIGN PATENT DOCUMENTS 2118437  10/1972  Germany.

OTHER PUBLICATIONS

Fabian et al., "A Theoretical Study of the Disulfide/Dithione Valence Isomerism", Collect Czech. Chem. Commun., 53, 2096–115, 1988.

Koreeda et al., "The Chemistry of 1,2–Dithiins: Synthesis of 1,2–Dithiin & 3,6–Disubstituted 1,2 Dithiins," Synlett, (3) 201–203, 1994.

Cimiraglia et al., 1991, "An ab initio study of the structure and electronic spectrum of 1,2–dithiete and 1,2–dithiin", J Mol Struct 230:287–293.

Aihara, 1990, "Chemical evolution, biosynthesis, and aromaticity", Bull Chem Soc Jpn 63:2899–2903.

Balza and Towers, 1990, "Dithiacyclohexadiene chlorohydrins and related sulphur containing polyynes from *Ambrosia chamissonis*", Phytochemistry 29(9):2901–2904.

Constabel and Towers, 1989, "The complex nature of the mechanism of toxicity of antibiotic dithiacyclohexadiene polyines (thiarubrines) from the asteraceae", Planta Medica 55:35–37.

Balza et al., 1989, "Dithiacyclohexadienes and thiophenes from *Ambrosia chamissonis*", Phytochemistry 28(12):3523–3524.

Schroth et al., 1967, "1,2–Dithiins, a new type of heterocycle", Angewandte Chemie Intl Ed in Engl 6(8):698∞699.

Schroth et al., 1966, "Stereoisomeric 1,4–dimercaptobutadienes", Chemical Abstracts issued Jan. 31, 1966, see abstract No. 64:3339a.

Freeman et al., 1993, "Naturally occurring 1,2–dithiins", in Reviews on Heteroatom Chemistry, S. Oae (ed.), 9:1–19.

Dzhemilev et al., 1986, "A new catalytic reaction of elemental sulfur with acetylenes by the action of cobalt complexes", Izv. Akad. Nauk SSSR, Ser. Khim 5:1211–1212.

Dzhemilev et al., 1987, "An original method for the preparation of sulfides and disulfides involving cobalt complexes", Izv. Akad. Nauk SSSR, Ser. Khim. 8:1918.

Freeman and Kim, 1989, "The Chemistry of 1,2–Dithiins," Sulfur Reports 9(3):207–256.

Primary Examiner—Richard L. Raymond
Assistant Examiner—Mary C. Cebulak
Attorney, Agent, or Firm—Pennie & Edmonds

[57] ABSTRACT

This invention pertains to a novel group of 1,2-dithiin compounds useful as antiinfective agents, and a novel synthetic process to produce the same. The compounds are particularly effective in treating fungal infections, especially those caused by *Candida albicans*, *Cryptococcus neoformans* or *Aspergillus fumigatus*.

16 Claims, No Drawings

1,2-DITHIIN ANTIINFECTIVE AGENTS

1. FIELD OF THE INVENTION

This invention pertains to a novel group of 1,2-dithiin heterocyclic substances that are useful as antifungal, antiinfective and cytotoxic agents. The invention further details a synthetic method for obtaining the substituted 1,2-dithiin ring system that has wide applicability in synthesis of derivatives.

2. BACKGROUND OF THE INVENTION 1,2-Dithiins are six-membered ring heterocyclic compounds having two contiguous CH groups of benzene replaced by two sulfur atoms. 1,2 Dithiin molecules have been the subject of intense investigations by theoretical chemists and spectroscopists due to their anti-aromatic non-planar ring system. Aihara, *J. Bull. Chem. Soc. Jpn.* 1990, 63, 2899–2903; Cirmiraglia, R. et al., *J. Mol. Str (Theochem)* 1991, 230, 287–293. Eight 1,2-dithiin-containing acetylenic compounds called thiarubrines have now been isolated from natural sources, primarily from the Asteraceae plants. Constabel, C. P.; Towers, G. H. N. *Planta Medica* 1989, 55, 35–37; Balza, F., et al., *Phytochemistry* 1990, 29, 2901; Towers G. H. N. et al., 1993, U.S. Pat. No. 5,202,348; Ellis, S., et al., *Phytochemistry* 1993, 33, 224–226. Among others of these eight, thiarubrine A (1) and thiarubrine B (2), isolated from the young leaves of *Aspilia mossambicesis* and *A. plurisetta*, have been shown to exhibit a wide spectrum of biological activity including antiviral and antibiotic activities. Balza, F. et al., *Phytochemistry* 1989, 28, 3523; Freeman, F. et al., *Sulfur Rep.* 1989, 9, 207–247; Freeman, F. *Heterocycles* 1990, 701–750; Schroth, W. et al., *Angew. Chem., Int. Ed. Engl.* 1967 6,698–699; Schroth, W. et al., *Chem.* 1965 5, 352∝353 and 353–354.

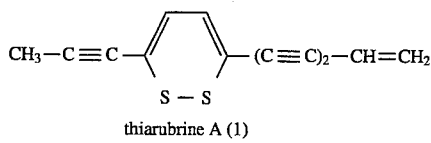

thiarubrine A (1)

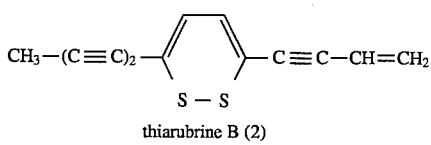

thiarubrine B (2)

It is well known that acetylenic compounds themselves, whether derived from nature Bohlman, F., et al., "*Naturally Occurring Acetylenes*" 1973, Academic Press, London, or from synthesis, Merz. et al., 1972, *Ger. Offen.* No. 2,118,437, have antiinfective as well as cytotoxic properties. All the natural 1,2-dithiins (thiarubrines) have polyacetylene side chains at either C-3-or C-3 and C-6. No total synthesis of any of the eight natural 1,2-dithiins containing acetylenes (thiarubrines) has been achieved, nor has any biological data of 1,2-dithiins without acetylenes been reported. The presence of acetylenic bonds in the thiarubrines makes their total syntheses difficult to achieve. Additionally, the role of the acetylenic bonds in their noted antifungal activity remains unclear. The inherent cytotoxicity as well the thermal and light instability of the thiarubrines severely limits their potential therapeutic utility as human medicinals. In order to overcome this shortcoming, a series of novel 1,2-dithiins were synthesized without acetylenic sidechains, and biologically evaluated for potential utility as antiinfective agents.

The first synthesis of 1,2-dithiin and its 3,6-disubstituted analogues was reported by Schroth and coworkers in Germany in 1960's. Schroth, W. et al., *Angew. Chem., Int. Ed. Engl.* 1967 6,698–699; Schroth, W. et al., *Chem.* 1965 5, 352–353 and 353–354. This method was most useful for the synthesis of diary dithiins (Scheme I). Thus, treatment of 1,4-diphenyl-1,3-butadiyne (3) with 2 equivalents of benzylthiol in refluxing ethanol in the presence of KOH provided the bis-benzylthiol adduct (4) in 85% yield with virtually complete stereo- and regioselectivity. Reductive removal of two benzyl groups by the treatment of 4 with Na in liquid ammonia at −78° C., followed by oxidative dithiin ring formation with $K_3[Fe(CN)_6]$ provided the deeply red-colored 3,6-diphenyl-1,2-dithiin (5) in about 51% overall yield.

Scheme I

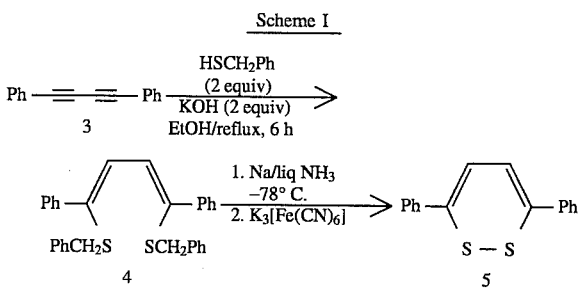

This method involving the reductive-removal of the benzyl group with sodium in liquid ammonia followed by oxidative ring closure with K3[Fe(CN) 6] is, however, less effective for the synthesis of 1,2-dithiins with non-aromatic substituents at 3- and 6-positions.

3. SUMMARY OF THE INVENTION

The invention is directed to novel dithiin compounds having antiinfective activity of the formula

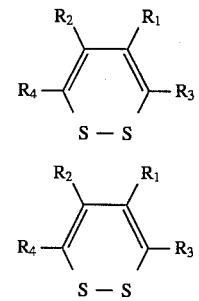

where
$R_1$ and $R_2$ are independently hydrogen, a halogen, an alkyl or alkenyl; and $R_3$ and $R_4$ are independently hydrogen, an alkyl or alkenyl;
wherein
the alkyl or alkenyl optionally contains cyclic groups, and is unsubstituted or substituted with at least one functional moiety selected from the group consisting of hydroxyl, halo, oxy, ether, carbonyl, carboxyl, mercapto, carbalkoxy, cyano, nitro, acyloxy, sulfamyl, amino, acylamino, carbamyl, aryl and aralkyl; the alkyl or alkenyl is preferably in the C1 to C20 size range.

the aryl and aralkyl groups are independently unsustitued or substituted with at least one functional moiety selected from the group consisting of hydroxyl, halo, ether, cyano, nitro, carboxy, carbalkoxy and amino; and $R_4$ and $R_2$, $R_2$ and $R_1$ or $R_1$ and $R_3$ are optionally linked together, and pharmaceutical acceptable salts thereof.

The substituted dithiin compound may have a structure wherein $R_4$ and $R_2$, $R_1$ and $R_1$ or $R_1$ and $R_3$ are linked through a moiety selected from the group consisting of carbonyl, carbamate, sulfate, sulfone, sulfonate, sulfonamide, phosphate, phosphonate, phosphonamide, ester, urea, thiourea and amides.

The following table summarizes some of the novel 1,2-Dithiins that have been synthesized and studied for their biological activity. We have labeled the compounds by alphabet for ease of discussion.

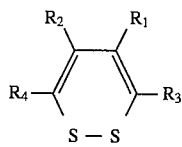

TABLE OF NOVEL 1,2-DITHIINS

| 1,2 Dithiin | $R_1$ | $R_2$ | $R_3$ | $R_4$ |
|---|---|---|---|---|
| A | H | H | $CH_2OH$ | $CH_2OH$ |
| B | H | H | $CH_2OCOCH_3$ | $CH_2OCOCH_3$ |
| c | H | H | $CH_3$ | $CH_2OH$ |
| D | H | H | $CH_2OCH_2OCH_3$ | $CH_2OCH_2OCH_3$ |
| E | H | H | CHO | CHO |
| F | H | H | $CH_2OCOPh$ | $CH_2OCOPh$ |
| G | H | H | $CH_2OCOCH_2CH_3$ | $CH_2OCOCH_2CH_3$ |
| H | H | H | $CH_2OCO$-i-Pr | $CH_2OCO$-i-Pr |
| I | H | H | $CH_2OCO$-cyclopropyl | $CH_2OCO$-cyclopropyl |
| J | H | H | $CH_2OCO$-cyclopropyl | $CH_2OH$ |

The invention is further directed to a novel method of synthesizing dithiin compounds described above wherein a 1,4-disubstituted diyne is reacted with benzylthiol in a basic solution to form a bis-benzylthiol adduct;

the bis-benzylthiol adduct is then separated from the basic solution by solvent extraction and crystallization distillation or chromatography;

the separated adduct is then reacted with an alkali metal in liquid ammonia to reductively remove the benzyl groups from the adduct to form the bisthiol;

the bisthiol is then oxidized by an oxidant to form the dithiin compound, with the proviso that the 1,4 disubstituted diyne is not 1,4 diaryl diyne.

The method is preferably carried out by using a basic solution comprising potassium hydroxide and ethanol; the metal sodium as the alkali metal; and $K_3[Fe(CN)_6]$ as the oxidant.

The method is preferably carried out by using a basic solution comprising potassium hydroxide and DMF; lithium as the alkali metal; and the oxidant comprising KI and $I_2$.

The invention is further directed to a novel method of treating an infection comprising administering to a warm blooded animal having such an infection with a therapeutically effective amount of a dithiin compound having a structure as described above.

The dithiin compound is particularly effective against fungal infection especially where the fungal infection is caused by *Candida albicans, Cryptococcus neoformans* or *Aspergillus fumigatus.*

The therapeutic effectiveness of the dithiin compound can be determined by a microdilution broth assay described below such that the MIC is less than 50 ug/ml is considered effective.

The dithiin compound may be administered topically, intravenously, orally, or intraperitoneally or by aerosol.

4. APPLICATIONS OF 1,2-DITHIINS

The novel 1,2-dithiins of the invention display strong antifungal activity, and are particularly effective in killing strains of Candida, Aspergillus and Cryptococcus.

The 1,2-dithiin compounds are advantageously used for treatment of various infections, in particular those caused by the type of organisms listed above. For example, the novel 1,2-dithiin designated 3,6-bis(hydroxymethyl)-1,2-dithiin has potent broad spectrum antifungal activity, which indicates a usefulness for in vivo medicinal therapy, i.e. in human patients. We have demonstrated in a series of biological tests which are shown below that the 1,2-dithiins containing no acetylene sidechains are potent inhibitors of *Candida albicans, Cryptococcus neoformans* and *Aspergillus fumigatus* at very low levels, without the co-occurring toxicity observed in the acetylene-containing thiarubrines.

5. METHODS

5.1 IN VITRO SUSCEPTIBILITY TESTS

In vitro susceptibility tests were performed to determine minimum inhibitory concentrations (MIC) and minimum fungicidal concentrations (MFC) of the following compounds: thiarubrine A, and the series of novel non-acetylenic 1,2-dithiin compounds described below. MIC tests were performed by a microdilution broth assay. The fungi tested were *Candida albicans* ATCC 10259 and strain B311, *Cryptococcus neoformans* ATCC 36556, *Aspergillus fumigatus* ATCC 13073, and *Trichophyton rubrum* ATCC 18762. The yeasts were propagated on yeast morphology agar, while the filamentous fungi were grown on Sabouraud's agar. All tests were performed in Sabouraud's broth in 96-well microliter plates, with compounds diluted serially, then inoculated with $2 \times 10^4$ cfu/ml for *C. albicans*, $4 \times 10^4$ cfu/ml for *C. neoformans*, $1 \times 10^3$ cfu/ml for *A. fumigatus*, and $1 \times 10^3$ cfu/ml for *T. rubrum* (all expressed as final concentrations). Plates were incubated at 30° C. for 48 h for all fungi except *T. rubrum*, which was incubated for 5 days. MIC's were read as the lowest concentration completely inhibiting growth. After MIC endpoints were determined, 50 ul portions were removed and plated on yeast morphology agar to detect viable organisms, and were incubated at 30° C. for 48 h. The MFC was determined to be the well with the lowest concentration resulting in no growth.

TABLE 1a

Results from Susceptibility Tests

MIC (ug/ml)

| Samples | C. albicans 10259 | C. albicans B311 | C. neoformans | A. fumigatus | T. rubrum | C. albicans 10259 | C. albicans B311 |
|---|---|---|---|---|---|---|---|
| Thia A | .15 | NT | .61 | .15 | NT | .30 | NT |
| Dithiin A | 16 | 31 | 2 | 16 | 16 | 63 | NT |
| Dithiin B | 3.1 | NT | .80 | .40 | NT | 6.3 | NT |
| Dithiin C | 12.5 | NT | NT | NT | NT | NT | NT |
| Dithiin D | 31 | 125 | 8 | 63 | 8 | >250 | 125 |
| Dithiin E | 8 | 8 | 4 | 8 | 4 | 8 | 8 |

NT - Not Tested

TABLE 1b

Results from Susceptibility Tests

MIC (ug/ml)

| Samples | C. albicans 10259 | C. albicans B311 | C. neoformans | A. fumigatus | T. rubrum |
|---|---|---|---|---|---|
| Thia A | .39 | NT | .78 | .10 | NT |
| Dithiin A | 25 | NT | 1.6 | 6.3 | NT |
| Dithiin B | 3.1 | NT | .80 | .20 | NT |
| Dithiin G | 12.5 | NT | 6.3 | 3.1 | NT |
| Dithiin H | >100 | NT | >100 | >100 | NT |
| Dithiin I | 6.3 | NT | 3.1 | 1.6 | NT |
| Dithiin J | 3.1 | NT | 1.6 | 0.8 | NT |

NT - NOT TESTED

5.2 DERMAL TOXICOLOGY TEST

Thiarubrine A and a new 1,2-dithiin compound 3,6-bis(hydroxymethyl)-1,2-dithiin were tested for the ability to elicit dermal irritation in ICR mice. Animals in groups of five each were lightly anesthetized, then the test substance, previously dissolved in aquaphor, was applied in the amount of 10 mg topically to the dorsal aspect of the right ear. Aquaphor without test substance was applied to the left ear as a control. Animals were inspected daily for five days for signs of dermal irritation and erythema, which was scored subjectively on a scale from 1 to 15, with 15 indicating severe toxicity.

5.3 SYSTEMIC TOXICOLOGY TEST

Thiarubrine A and the novel 3,6-bis(hydroxymethyl)-1,2-dithiin have also been evaluated for their systemic toxicity potential. ICR mice, in groups of five or six each were injected with solutions of the test compound given intraperitoneally for three consecutive days for thiarubrine A and five consecutive days for the 1,2-dithiin. Animals were weighed daily and observed for mortalities over a 14 day period. An $LD_{50}$ of 0.6 mg/kg for thiarubrine A was determined. 3,6-Bis(hydroxymethyl)-1,2-dithiin given by the same route at doses up to 30 mg/kg was non-toxic, with no apparent weight loss when compared to controls.

5.4 BIOLOGICAL ACTIVITY OF THE 1,2-DITHIINS

Results for the MIC and MFC determinations are presented in Tables 1a and 1b. As can be seen, the results indicate that the previously unknown 1,2-dithiin compounds have good in vitro activity, with results for the more active members of the series similar to those obtained with thiarubrine A. Importantly, the MFC's for all of the tested compounds were, in general, within one dilution of the MIC, indicating a fungicidal mechanism of action. The results indicate potent antifungal activity of the new non-acetylenic 1,2-dithiin compounds against a broad spectrum of medically important fungi.

Results from the dermal irritation test (see Table 2) showed that by day 5, acetylene-containing thiarubrine A elicited pronounced toxicity, with an average score of 9 for the treated ear and a normal reading of 4 for the control ear for the five animals. In contrast, the mice treated with the 1,2-dithiin lacking acetylene side chains (3,6-bis(hydroxymethyl)- 1,2-dithiin) exhibited no signs of dermal irritation or erythema over the five-day period.

Results from the systemic toxicological study showed thiarubrine A to be highly toxic, with an $LD_{50}$ dose of approximately 0.6 mg/kg (1.8 mg/kg for total dose), whereas all mice given 3,6-bis(hydroxymethyl)- 1,2-dithiin by the same route survived a daily dose of 30 mg/kg (150 mg/kg total) and had no apparent loss in weight in comparison to controls.

Overall, the results indicate that the 1,2-dithiin class of compounds has a potent antifungal profile without the adverse toxicological properties of the acetylene-containing thiarubrines. This substantiates that the acetylene moieties found within the thiarubrine class are responsible for much of the observed thiarubrines toxicity. Also, the acetylenic moieties are only partly responsible for the antiinfective properties with the 1,2-dithiin ring being the important pharmacophore for antiinfective activity.

TABLE 2

| Group | Day 2 | | Day 2 | | Day 3 | | Day 4 | | Day 5 | |
|---|---|---|---|---|---|---|---|---|---|---|
| | Control | Treated | Control | Treated | Control | Treated | Control | Treated | Control | Treated |
| Thia A | 4 | 4 | 4 | 6 | 4 | 7 | 4 | 9 | 4 | 9 |
| Dithiin A | 4 | 4 | 4 | 4 | 4 | 4 | 4 | 4 | 4 | 4 |

EXAMPLE 1

Benzylthiol Addition to 1,6-Dihydroxy-2,4-hexadiyne

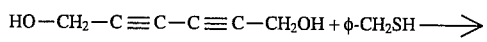

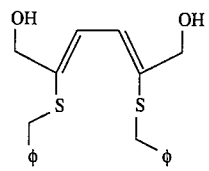

A 100 ml round-bottomed flask was charged with 40 mL of DMF, 1 mL of water, and 300 mg of KOH pellets. To this mixture was added 2.59 mL of benzylthiol (22 mmol, 2.2 equiv). After stirring at rt for 20 min, 1.10 g of 1,6-dihydroxy-2,4-hexadiyne (I) (10 mmol) was added to the solution, which became hot (the flask was cooled in the water bath) and immediately turned deep red. The reaction mixture was then stirred at rt for 3 h and was then poured into 150 mL of water. The resulting mixture was extracted with EtOAc (1×200 mL, 1×100 mL) and then the combined EtOAc layers were washed successively with water (2 times) and brine and were dried (MgSO$_4$). Evaporation of the solvent under reduced pressure provided a slightly yellow solid residue, which upon recrystallization from hexanes/CHCl3/EtOAc gave 2.34 g (65%) of pale yellow bis-benzylthiol adduct 11: mp 121.5°–123° C.; Rf 0.36 (EtOAc/hexanes 1:1); $^1$H NMR (300 MHz, CDCl$_3$) δ1.65 (t,2H, J=6.3 Hz), 3.90 (s, 4H), 4.15 (d, 4H, J=6.3 Hz), 6.81 (s, 2H), 7.22–7.29 (m, 10H); $^{13}$C NMR (75 MHz, CDCl$_3$) δ37.70 (t), 66.42 (t), 127.19 (d), 128.58 (d), 128.86 (d), 129.08 (d), 137.95 (s), 138.24 (s); IR (KBr) 3422, 3388, 3061, 2925, 1548 cm$^{-1}$.

Anal. Calcd for $C_{20}H_{22}O_2S_2 \cdot \frac{1}{2}H_2O$: C, 65.36; H, 6.31. Found C, 65.73; H, 6.23

EXAMPLE 2

3,6-Bis(hydroxymethyl)-1,2-dithiin (Dithiin A)

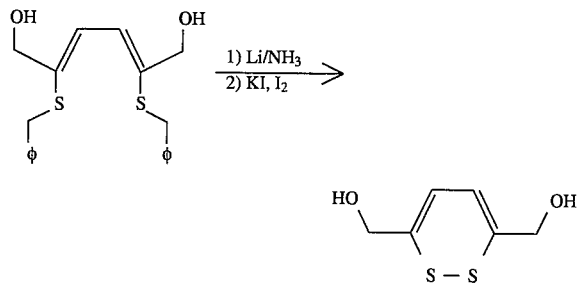

A 25 mL, three-necked, round-bottomed flask equipped with a reflux condenser and two rubber septa was charged with about 10 mL of liquid ammonia at −78° C. To this liquid ammonia were added at that temperature, first 42 mg (4 equiv) of lithium and then 538 mg of diol (II) in 4 mL of dry THF. Soon after the completion of the additions of the diol solution, the blue color of the solution disappeared and the mixture became a white suspension. An additional amount of lithium was added in order to maintain the blue color of the mixture. The resulting mixture was stirred for I h at −78° C., at which time several drops of MEOH was added until the blue color disappeared. The reaction mixture was allowed to gradually warm up to rt, during which time the ammonia was removed by evaporation to afford a yellow solution. The remaining ammonia was removed by rotary evaporation. The resulting residue was treated, while stirring, with 6 mL of water and 10 mL of ether and the resulting mixture was cooled to 0° C. and was treated with 761 mg of iodine (3.00 mmol, 2.9 equiv) dissolved in 15 mL of 20% aqueous KI. The mixture was then allowed to warm up to rt and the deep-red ether and the orange aqueous layers were separated. The aqueous layer was extracted with ether (2×20 mL) and the combined ether layers were washed successively with 0.1M aqueous Na$_2$SO$_4$ (15 mL), water (20 mL), and brine (20 mL) and were finally dried (Na$_2$SO$_4$). Removal of the solvent by rotary evaporation followed by purification by silica gel flash column chromatography with EtOAc/hexanes (1:1) as the eluent afforded 125 mg of 3,6-bis(hydroxymethyl)-1,2-dithiin (47%) as a red solid: mp 64°–66° C. (chloroform/hexanes); Rf 0.14 (EtOAc/hexanes 1:1); $^1$H NMR (360 MHz, -CDCl$_3$) δ1.77 (t, 2H, J=6.2 Hz), 4.29 (d, 4H, J=6.2 Hz), 6.40 (s)lH); 13C NMR (90 MHz, CDCl$_3$) δ64.63 (t), 125.17 (d), 134.96 (s). Anal. Calcd for $C_6H_8O_2S_2$: C, 40.89; H, 4.58. Found: 0, 41.06; H, 4.71

EXAMPLE 3

3,6-Bis(acetyloxymethyl)-1,2-dithiin (Dithiin B)

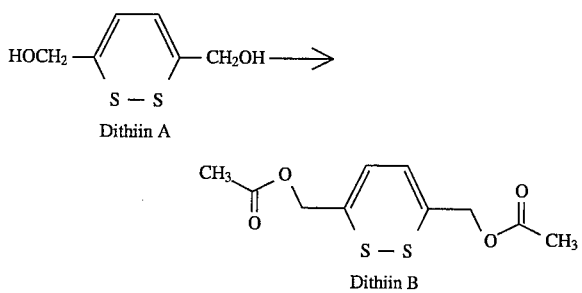

To a stirred solution of 3,6-bis(hydroxymethyl)-1,2-dithiin, Dithiin A (600 mg, 3.40 mmol) in pyridine (15 mL) was added dropwise acetic anhydride (2.0 mL, 1000 mol %). After stirring overnight in the dark the mixture was diluted with diethyl ether (200 mL) and partition between diethyl ether (50 mL) and 3.0M $H_3PO_4$ (200 mL). The diethyl ether layer was washed with 3.0M $H_3PO_4$ (200 mL), saturated $NaHCO_3$ (200 mL), dried ($Na_2SO_4$), and the solvent was removed by rotary evaporation. The resulting oily residue was purified by silica gel flash column chromatography using 1:3/diethyl ether:hexane as eluants to give 40 mg Dithiin B as a red oil (870 mg): $^1$H NMR ($CDCl_3$) δ6.38 (s, 2H), 4.70 (s, 4H), 2.10 (s, 6H); 13C NMR 6 170.37, 130.48, 127.75, 65.19, 20.77.

EXAMPLE 4

3,6-Bis(benzoyloxymethyl)-1,2-dithiin, (Dithiin F)

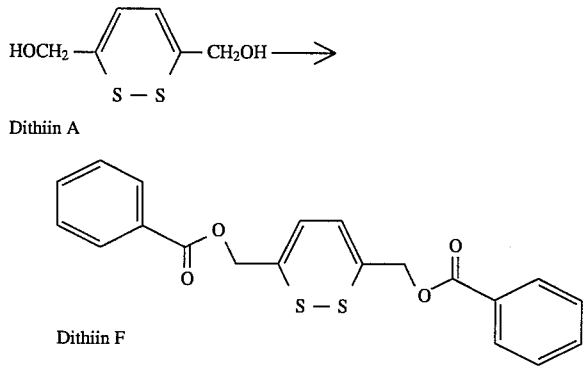

To a stirred solution of 3,6-bis(hydroxymethyl)- 1,2-dithiin, Dithiin A (20 mg, 0.1 13 mmol) in pyridine (1.0 mL) was added in one portion benzoyl chloride (0.13 mL). After stirring in the dark at room temperature overnight the mixture was diluted with diethyl ether (10 mL) and partitioned between 3.0M $H_3PO_4$ (20 mL) and diethyl ether (5.0 mL). The diethyl ether layer was washed with saturated $NaHCO_3$ (20 mL), dried ($Na_2SO_4$), and the solvent was removed by rotary evaporation. The resulting oily residue was purified by silica gel flash column chromatography using 1:3/diethyl ether:hexane as eluants to give a red oil (40.1 mg): $^1$H NMR ($CDCl_3$) 6 8.07 (d, 4H), 7.59 (t, 2H), 7.46 (t, 4H), 6.50 (s, 2H), 4.98 (s, 4H); $^{13}$C NMR δ165.91, 133.37, 130.63, 129.78, 128.55, 128.49, 127.70, 65.65.

EXAMPLE 5

3,6-Bis (propionyloxymethyl)-1,2-dithiin, (Dithiin G)

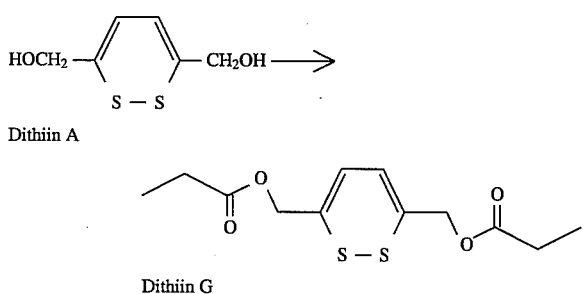

To a stirred solution of 3,6-bis(hydroxymethyl)- 1,2-dithiin, Dithiin A (20 mg, 0.113 mmol) and triethylamine (0.30 mL) in tetrahydrofuran (2.0 mL) was added dropwise propionyl chloride until the entire mixture turned solid. To this solidified mixture was added 1.0M $H_3PO_4$ (20 mL) and the target compound was extracted with diethyl ether (2×20 mL). The combined ether extracts were washed with saturated $NaHCO_3$ (100 mL), dried ($Na_2SO_4$), and evaporated to give a red oil (22.2 mg): $^1$H NMR ($CDCl_1$) δ6.38 (s, 2H), 4,72 (s, 4H), 2.39 (q, 4H), 1.16 (t, 6H).

EXAMPLE 6

3,6-Bis(isobutyryloxymethyl)-1,2-Dithiin, (Dithiin H)

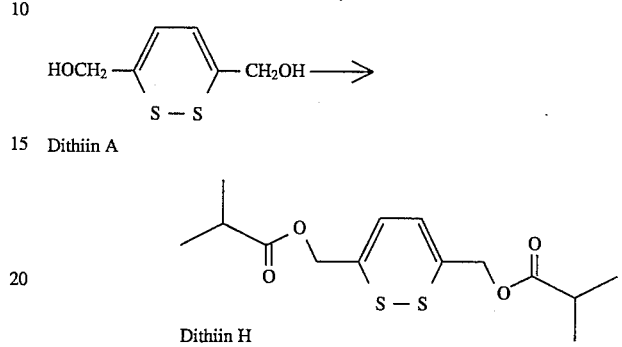

To a stirred solution of isobutyric anhydride (0.2 mL, 1,000 mol %) in pyridine (2.0 mL) was added in one portion solid 3,6-bis(hydroxymethyl)-1,2-dithiin, Dithiin A (20 mg, 0.113 mmol). After stirring in the dark at room temperature overnight the mixture was diluted with diethyl ether (20 mL) and partitioned between 3.0M $H_3PO_4$ (80 mL) and diethyl ether (30 mL). The diethyl ether layer was washed with saturated $NaHCO_3$ (100 mL), dried ($Na_2SO_4$), and evaporated to give the product as a red oil (32 mg): 1H NMR ($CDCl_3$) δ6.37 (s, 2H), 4.71 (s, 4H), 2.60 (m, 2H), 1.19 (d, 6H).

EXAMPLE 7

3,6-Bis(cyclopropanecarbonyloxymethyl)-1,2-dithiin (Dithiin I)

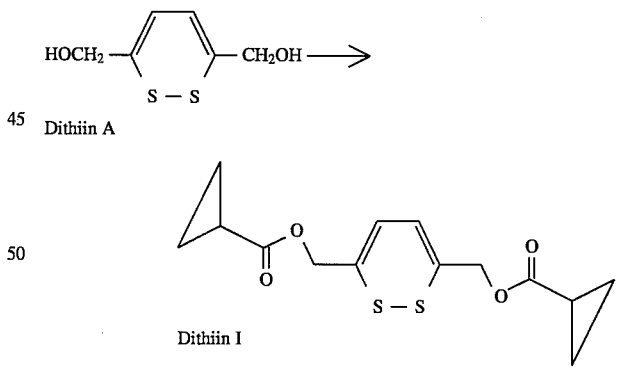

To a stirred solution of triethylamine (0.30 mL) in tetrahydrofuran (2.0 mL) at 0° C. was added dropwise cyclopropanecarbonyl chloride (0.10 mL) followed by the addition of 3,6-bis(hydroxymethyl)-1,2-dithiin, Dithiin A (20 mg, 0.113 mmol) in tetrahydrofuran (1.0 mL). After stirring in the dark at room temperature overnight the mixture was diluted with ether (20 mL) and partitioned between 1.0M $H_3PO_4$ (80 mL) and diethyl ether (30 mL). The diethyl ether layer was washed with saturated $NaHCO_3$ (100 mL), dried ($Na_2SO_4$), and evaporated to give a red oil (31.5 mg): $^1$H NMR ($CDCl_3$) δ6.38 (s, 2H), 4.71 (s, 4H), 1.67 (m, 2H), 1.04 (m, 4H), 0.92 (m, 4H).

EXAMPLE 8

3,6-Bis[methoxymethyloxy)methyl]-1,2-diothiin (Dithiin D)

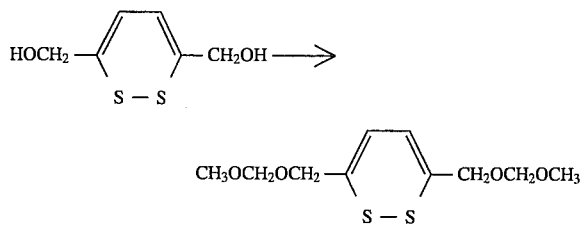

To a cooled (0° C.) Solution of 18.7 mg. of diol Dithiin A and 185 μL of N,N-diisopropylethylamine (10 mol. equiv) in 2 mL of dry methylene chloride was added in one portion 48.4 μL of methoxymethyl chloride (6.0 mol equiv). After stirring at room temperature overnight, the solution was diluted with methylene chloride (30 mL) and the resulting mixture was washed first with water (20 mL) and then with brine (20 mL). The organic layer was dried ($MgSO_4$) and the crude product obtained upon rotary evaporation of the solvent was purified by silica gel flash column chromatography with hexanes/$CHCl_3$/EtOAc (5:5:1) as the eluent, providing 25.2 mg of methoxymethyl ether Dithiin D (90% yield) as an orange red viscous liquid): Rf 0.45 (EtO/Ac/hexanes 1:4) $Na_2SO_4$); $^1H$ NMR (360 MHz, $CDCl_3$) δ3.40 (s,6H),4.22(s,4H),4.67(s,4H), 6.36(s,2H); $^{13}C$ NMR (90 MHZ, $CDCl^3$) δ55.54(q), 68.83 (t), 95.76(t), 126.45(d), 132.34(s).

EXAMPLE 9

3,6-Diformyl-1,2-dithiin (Dithiin E)

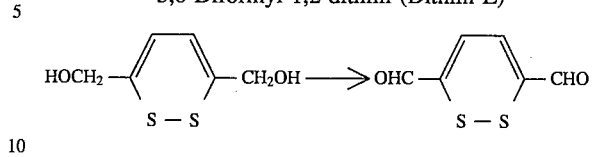

To a suspension of 19.4 mg of diol Dithiin A in 2 mL of methylene chloride was added at room temperature in one portion 102 mg of 1,1,1-triacetoxy-1,1-dihydro-1,2-benziodoxol-3(1H)-one (Dess-Martin's reagent). After stirring at that temperature for 40 min., the reaction mixture was treated with 100 mg of $Na_2S_2O_3$ in 15 mL of saturated aqueous $NaHCO_3$. The resulting mixture was extracted with methylene chloride (2×15 mL) and the combined organic layers were washed with brine (20 mL) and dried ($MgSO_4$). The crude product obtained upon rotary evaporation of the solvent was purified by silica gel flash column chromatography with EtOAc/hexanes 1:1 as the eluent, providing 18.5 mg (>98%) of dialdehyde Dithiin A as deep purple crystals: mp 56°–58° C.,Rf 0.23 (EtOAc/hexanes 1:1); $^1H$ NMR (360 MHz, $CDCl_3$) δ7.30 (s,2H),9.60 (s,2H); $^{13}C$ NMR (90 MHz, CDCl3) δ141.52(d),142.05(s), 186.54(d);IR (KBr) 3050, 2958, 2925, 2851, 1670 $cm^{-1}$; UV ($CHCl_3$) $\lambda_{max}$ 557 (ε 2,250) and 281 nm (ε 29,400). Anal. Calcd for $C_6H_4S_2O_2$: C,41.84; H, 2.34. Found: C, 41.84; H, 2.49.

General Flow Sheet

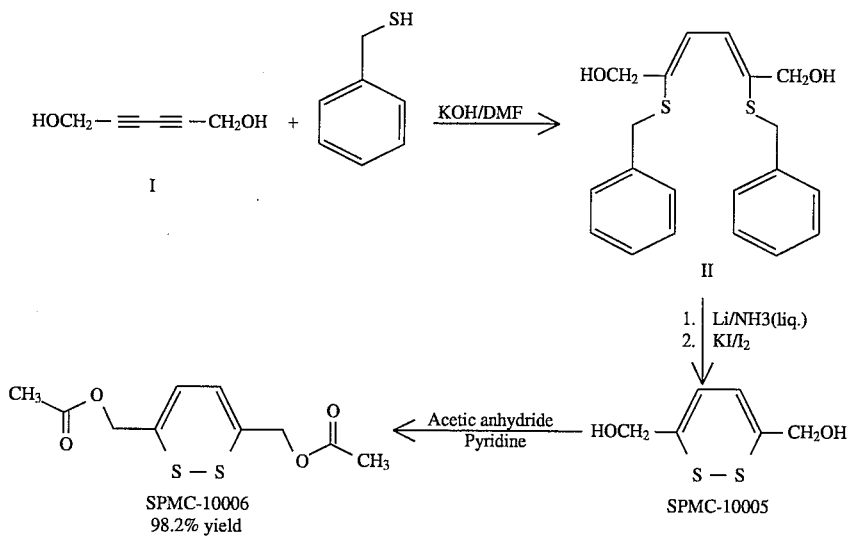

-continued
General Flow Sheet

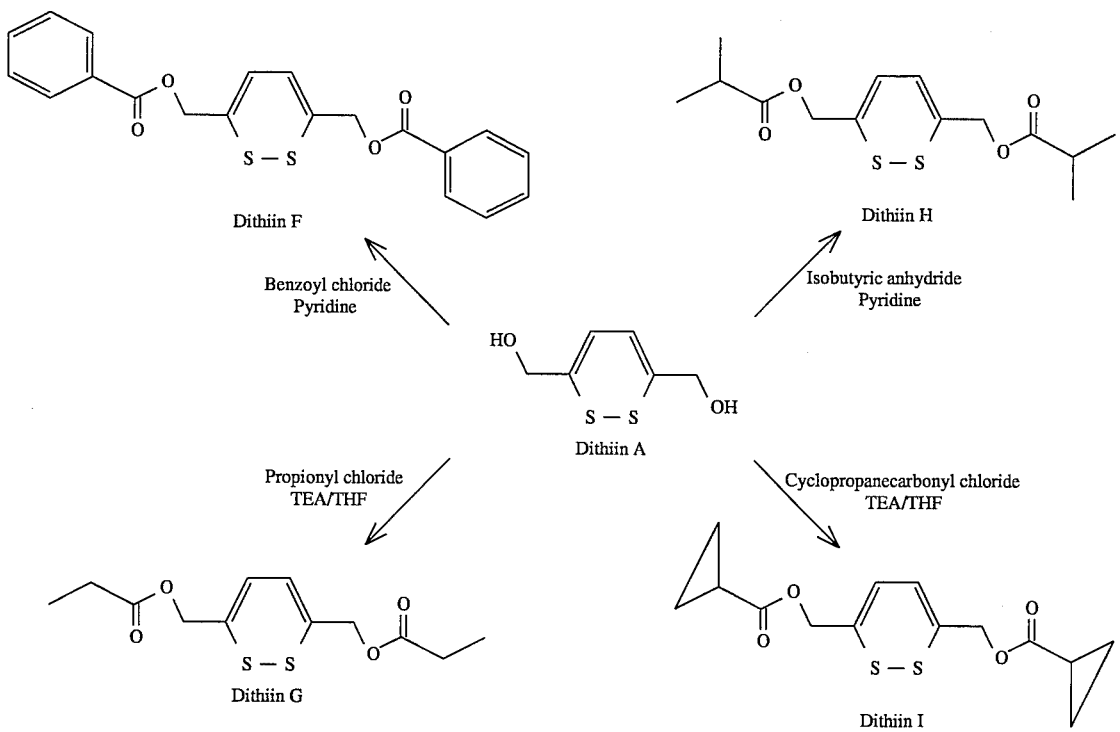

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed is:

1. A dithiin compound having the formula:

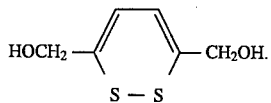

2. A dithiin compound having the formula:

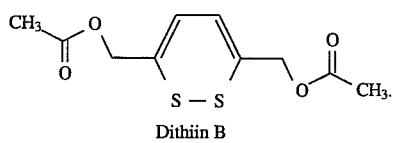

Dithiin B

3. A dithiin compound having the formula:

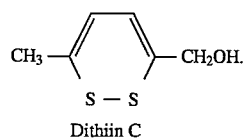

Dithiin C

4. A dithiin compound having the formula:

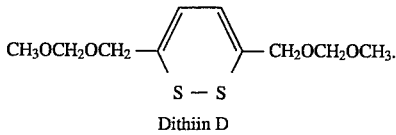

Dithiin D

5. A dithiin compound having the formula:

Dithiin E

6. A dithiin compound having the formula:

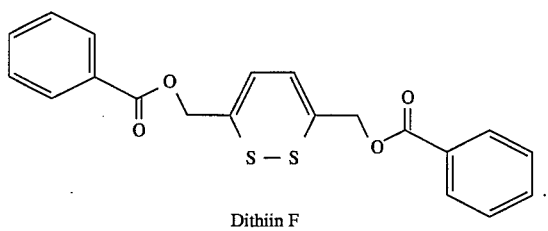

Dithiin F

7. A dithiin compound having the formula:

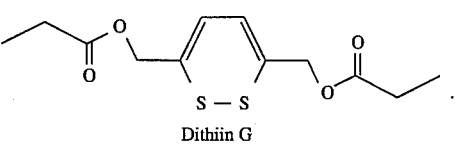

Dithiin G

8. A dithiin compound having the formula:

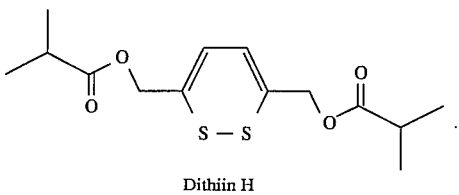

Dithiin H

9. A dithiin compound having the formula:

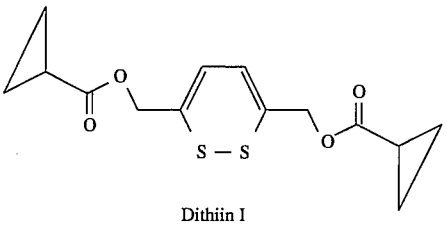

Dithiin I

10. A dithiin compound having the formula:

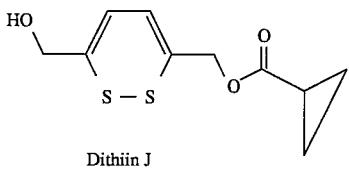

Dithiin J

11. A 3,6-disubstituted dithiin compound synthesized by the process comprising the steps of:

reacting a 1,4-disubstituted diyne with the compound benzylthiol in a basic solution comprising potassium hydroxide and DMF to form a bis-benzylthiol adduct;

separating the bis-benzylthiol adduct from the basic solution by solvent extraction and crystallization;

reductively removing from the separated adduct the unsubstituted benzyl groups with lithium in liquid ammonia to form the bisthiol;

oxidizing the bisthiol with an oxidant comprising KI and $I_2$ to form the dithiin compound, with the proviso that the 1,4 disubstituted diyne is not 1,4 diaryl diyne.

12. A dithiin compound synthesized by the process of acylating the 3,6-bis(hydroxy methyl)-1,2-dithiin.

13. A method of treating a fungal infection comprising administering an effective amount of a dithiin compound of the formula:

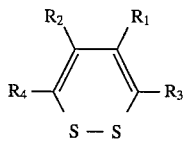

where $R_1$ and $R_2$ are hydrogen;

$R_3$ and $R_4$ are independently selected from the group consisting of alkyl and alkenyl, wherein said alkyl and alkenyl is optionally cyclic, and is optionally substituted with at least one functional moiety selected from the group consisting of hydroxyl, halo, oxy, ether, carbonyl, carboxyl, mercapto, carbalkoxy, cyano, nitro, acyloxy, sulfamyl, amino, acylamino, carbamyl, aryl and aralkyl, wherein the aryl and aralkyl groups are independently unsubstituted or substituted with at least one functional moiety selected from the group consisting of hydroxyl, halo, ether, cyano, nitro, carboxy, carbalkoxy and amino;

or a pharmaceutically acceptable salt thereof.

14. The method of claim 13, wherein said fungal infection is caused by *Candida albicans, Cryptococcus neoformans* or *Aspergillus fumigatus*.

15. The method of claim 14 wherein the effectiveness of the dithiin compound is determined by a microdilution broth assay such that the MIC is less than 50 ug/ml.

16. The method of claim 13, wherein said dithiin compound is selected from the group consisting of:

3,6-Bis(hydroxymethyl)-1,2-dithiin;
3,6-Bis(acetyloxymethyl)-1,2-dithiin;
3-Hydroxymethyl-6-methyl-1,2-dithiin;
3,6-Bis[methoxymethyloxy)methyl]-1,2-dithiin;
3,6-Diformyl-1,2-dithiin;
3,6-Bis(propionyloxymethyl)-1,2-dithiin;
3,6-Bis(isobutyryloxymethyl)-1,2-dithiin;
3,6-Bis(cyclopropanecarbonyloxymethyl)-1,2-dithiin; and
3-Hydroxymethyl-6-cyclopropanecarbonyloxymethyl-1,2-dithiin.

* * * * *

UNITED STATES PATENT AND TRADEMARK OFFICE
CERTIFICATE OF CORRECTION

| | | |
|---|---|---|
| PATENT NO. | : | 5,556,875 |
| DATED | : | September 17, 1996 |
| INVENTOR(S) | : | Thien V. Truong, Donald E. Bierer, Jeffrey M. Dener, Richard Hector, Michael S. Tempesta, Bernard Loev, Wu Yang and Masato Koreeda |

It is certified that error appears in the above-identified patent and that said Letters Patent is hereby corrected as shown below:

Title page, item [22], should read -- Filed: August 24, 1993--.

Signed and Sealed this

Seventh Day of April, 1998

Attest:

BRUCE LEHMAN

*Attesting Officer*          *Commissioner of Patents and Trademarks*